United States Patent [19]

Chong

[11] Patent Number: 4,922,895

[45] Date of Patent: May 8, 1990

[54] ORTHOSIS FOR METATARSUS ADDUCTUS

[76] Inventor: Andrew Chong, 1632 Hemstock Ave., Wheaton, Ill. 60187

[21] Appl. No.: 677,372

[22] Filed: Dec. 3, 1984

[51] Int. Cl.⁵ ............................................. A61F 3/00
[52] U.S. Cl. .................................. 128/80 J; 128/80 R
[58] Field of Search ...................... 128/80 J, 87 R, 90, 128/80 R, 80 E

[56] References Cited

U.S. PATENT DOCUMENTS

| | | | |
|---|---|---|---|
| 114,669 | 5/1871 | Grant | 128/80 J |
| 1,012,017 | 12/1911 | Salt | 128/80 J |
| 1,691,235 | 11/1928 | Fischer | 128/80 J |
| 2,474,634 | 6/1949 | Mason | 128/89 R |
| 2,523,606 | 9/1947 | Young | 128/87 R |
| 2,889,827 | 6/1959 | Basso | 128/87 R |
| 3,308,829 | 3/1967 | Edwards | 128/80 J |
| 3,548,820 | 12/1970 | Bergen | 128/89 R |
| 3,618,946 | 11/1971 | Lee et al. | 128/80 R |
| 3,680,549 | 8/1972 | Lehneis et al. | 128/80 E |
| 3,916,886 | 11/1975 | Rogers | 128/80 E |
| 3,973,559 | 8/1976 | Reiman | 128/80 J |
| 3,976,059 | 8/1976 | Lonardo | 128/80 E |
| 4,006,741 | 2/1977 | Arluck | 128/90 |
| 4,289,122 | 9/1981 | Mason et al. | 128/80 E |
| 4,349,016 | 9/1982 | Glassman et al. | 119/96 X |
| 4,351,324 | 9/1982 | Bronkhorst | 128/80 J |
| 4,382,439 | 5/1983 | Shen | 128/89 R |
| 4,454,871 | 6/1984 | Mann et al. | 128/90 |
| 4,505,269 | 3/1985 | Davies et al. | 128/87 R |

FOREIGN PATENT DOCUMENTS 2651469  5/1978  Fed. Rep. of Germany ..... 128/80 J
3228753  2/1984  Fed. Rep. of Germany ..... 128/80 J Primary Examiner—Kenneth J. Dorner
Assistant Examiner—J. R. Hakomaki
Attorney, Agent, or Firm—Allegretti & Witcoff, Ltd.

[57] ABSTRACT

A brace made of rigid thermoplastic material that retains the corrective features of a corrective cast without the disadvantages of a cast. The brace securely encloses the heel and the medial portion of the foot up to or slightly beyond the tip of the big toe on the medial side only. A strap, adjustably secured to the brace, directs a corrective force on the apex of the deformity on the lateral aspect of the foot, thus effecting correction. The brace has a leg-embracing component which includes a strap for preventing the heel from pulling away from the brace.

6 Claims, 3 Drawing Sheets

ORTHOSIS FOR METATARSUS ADDUCTUS

BACKGROUND OF THE INVENTION

There are numerous causes of intoeing in children, including metatarsus adductus, clubfeet, and internal tibial torsion. The device of the present invention is designed specifically for the treatment of metatarsus adductus only.

Metatarsus adductus is a congenital condition in which the forefoot is adducted or turned in relativeto the hindfoot or heel. The primary treatment is corrective casting, which gives excellent results. However, it has serious disadvantages, including repeated expensive castings, skin pressure problems, and potentially diastrous vascular problems.

Alternatives to casting have been sought over the years, and they basically fall into two groups: shoes (or boots) and braces (or splints). In spite of several introductions over the years, these alternatives have not been utilized to any significant degree, and casting remains even today the treatment of choice. The reason is that these alternatives lack the features that enable them to correct the deformity.

Shoes and boots have been ineffective in obtaining correction because, being all enclosing, they do not provide enough pressure at specific points to effect correction. At the present time shoes are used mainly as a holding device after correction has been obtained with casts.

The braces and splints that have been introduced so far do not hold the heel and the medial portion of the foot securely enough to allow for successful correction of the deformity; for example, U.S. Pat. Nos. 3,924,615 to McKim; 3,812,850 and 3,910,267 to Reiman; and the brace designed by Lusskin as reported in *The Journal of Bone and Joint Surgery,* January 1951, p. 269. All these devices use straps to hold the medial portion of the foot, which is insufficient for correction.

U.S. Pat. No. 3,973,559 to Reiman attempts to address the problem by adding a wall along the medial side of the footplate. This patent is believed to be the closest prior art. However, it still does not hold the medial portion of the foot securely enough to effect correctoion, and lacks several important features that determine success or failure:

(1) The medial wall extends only to the base of the big toe, and depends on the child wearing both footplates attached together in an angular relationship, and the child lying prone (on his stomach), and the mattress on which the child lies, to effect correction of the bit toe varus, which is an important component of the deformity. Hence, the splint has cumbersome constraints of wearing both footplates even if only one foot is affected, and of posture since the child has to be lying prone.

(2) The medial wall does not have an upper ledge to prevent dorsal migration of the big toe and medial portion of the forefoot, thus escaping from the corrective influence of the medial wall. This is very important if one realizes how wiggly the infant foot can be.

(3) The medial wall is straight. This is much less effective than a slightly convex border (abducted position) which allows the foot to be placed in a slightly over-corrected position.

(4) The splint does not have rigid support for the lateral aspect of the heel to prevent valgus (turning out) of the heel, a complication to be avoided in the treatment of metatarsus adductus.

BRIEF SUMMARY OF THE INVENTION

The present invention is a brace preferably made of rigid thermoplastic material which securely encloses the heel and medial portion of the foot up to or slightly beyond the tip of the big toe. The invention embodies the three-point fixation principle. By holding the heel and the medial portion of the forefoot and great toe securely, the brace fixates the adducted foot at two points—the heel, which becomes the first point of fixation, and the base of the bit toe, which forms the second point of fixation. When these two points of fixation are secure, the third point of fixation can then be applied between the first two points by means of a strap which directs a corrective force on the apex of the convexity of the deformity on the lateral aspect of the foot, thus effecting correction.

DESCRIPTION OF THE DRAWINGS

For illustrative purposes, the brace for the left foot only is shown.

DESCRIPTION OF THE INVENTION

The brace is designed for application to the foot with metatarsus adductus (forefoot adduction) to effect correction.

Figure 1:
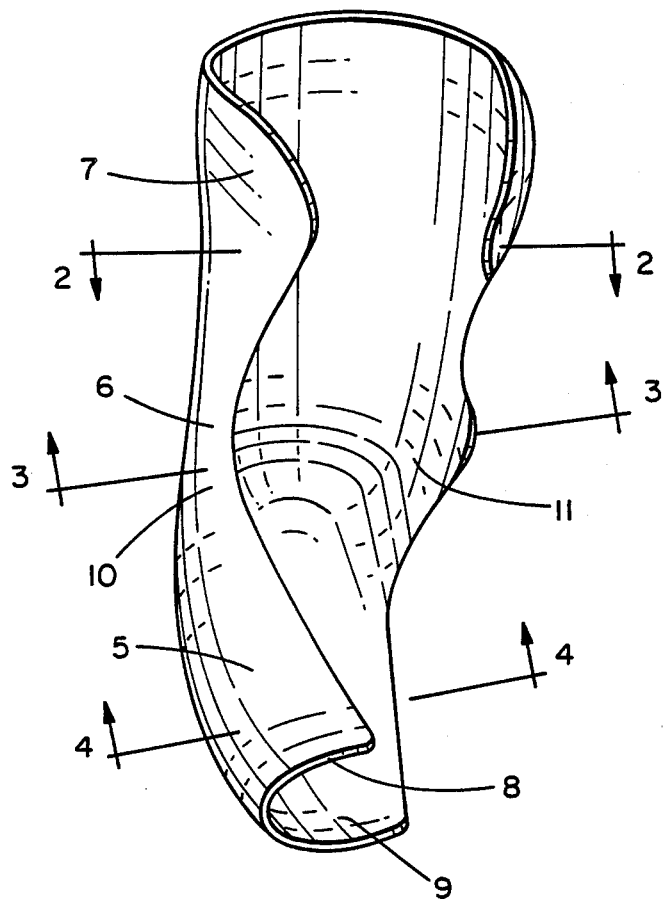
FIG. 1 is a perspective anterior view of the brace of the invention without straps.
Figure 2:
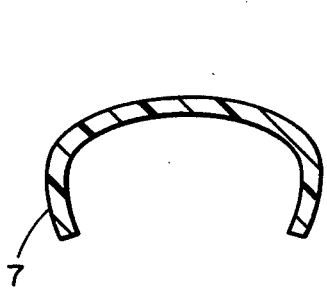
FIG. 2 is a cross-sectional view taken on line 2—2 of FIG. 1.
Figure 4:
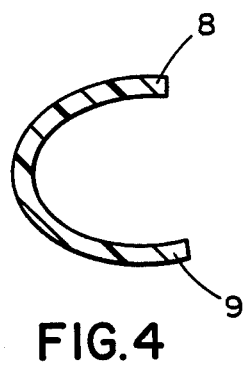
FIG. 4 is a cross-sectional view taken on line 4—4 of FIG. 1.
Figure 5:
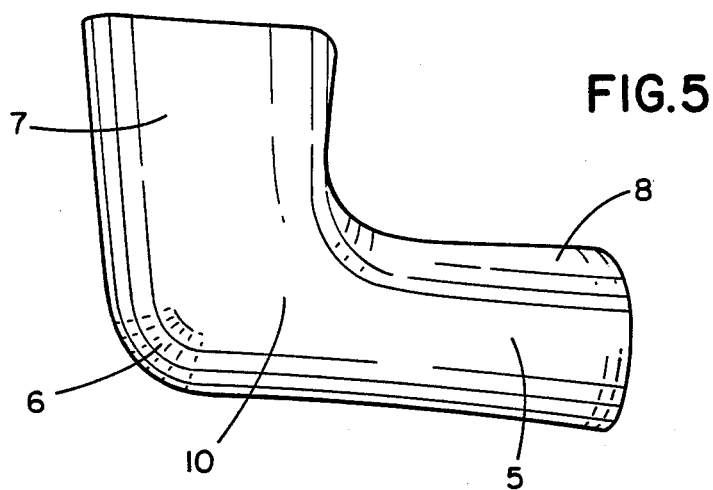
FIG. 5 is a medial elevation view of the brace.
Figure 6:
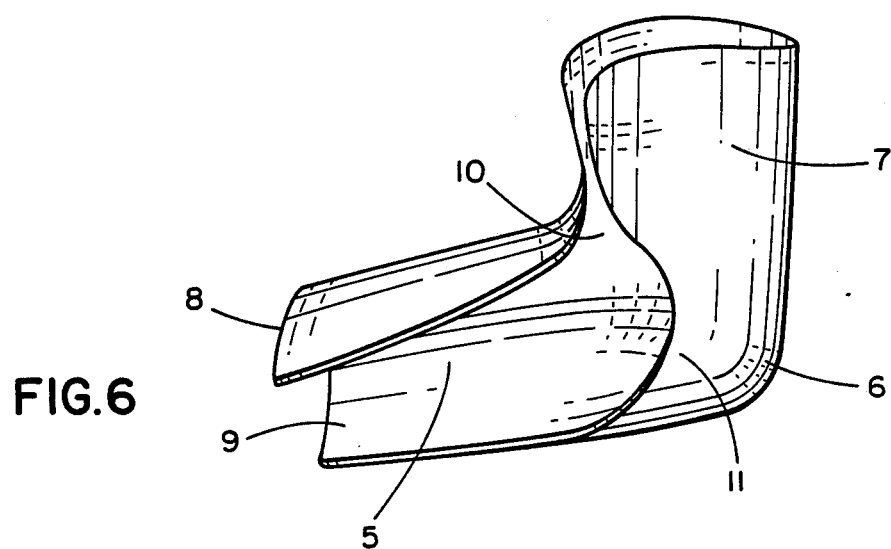
FIG. 6 is a lateral elevational view.
Figure 7:
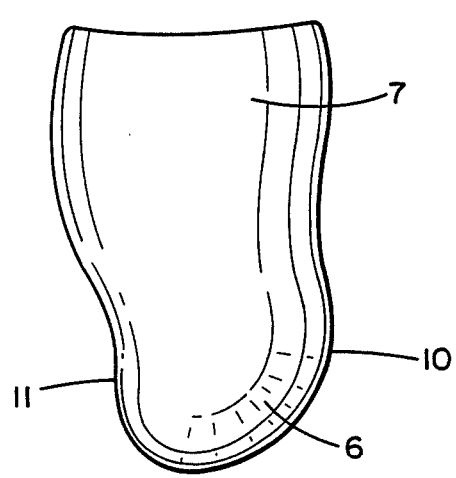
FIG. 7 is a posterior elevational view.
Figure 8:
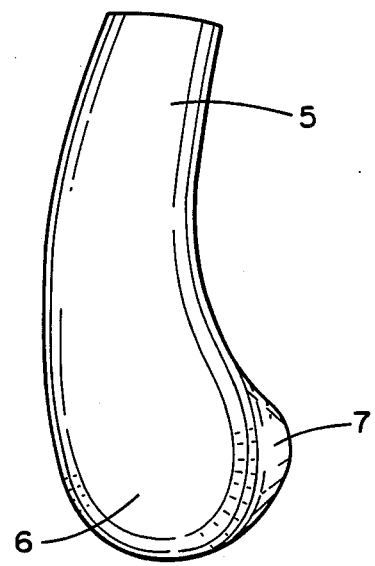
FIG. 8 is a bottom view.

Referring to FIG. 1, the brace is made of a molded thermoplastic material, and consists of a foot component 5, a heel component 6, and a leg component 7 that hold the foot in the corrected position. The foot component 5 extends from the heel to the tip of the big toe or slightly beyond. This is important because hallux varus (turning in of the big toe) is a component of the metatarsus adductus deformity, and correction must include the big toe as well as the foot. The foot component 5 is C-shaped in cross-section (refer to FIG. 4), and embraces the sole and the top of the foot on the medial side only. On the dorsal (upper) aspect, an upper ledge 8 extends laterally to cover the medial portion of the foot as well as the first two toes. On the plantar (lower) aspect, a lower ledge 9 extends laterally to cover the medial part of the sole of the foot and the medial two toes. Horizontal edges 8,9 are important because they hold the forefoot securely between them, and prevent the big toe and forefoot from migrating upwards or downwards during correction, and thus escaping from the corrective influence of foot component 5. Horizontal edges 8,9 must not reach to the lateral border of the foot. If they do, the corrective force (described below) cannot be utilized.

It should also be noted that foot component 5 is not perfectly straight, but slightly convex medially (abducted) to allow for over-correction if necessary.

Figure 3:
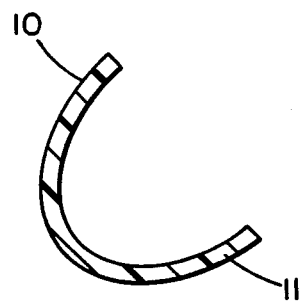
FIG. 3 is a cross-sectional view taken on line 3—3 of FIG. 1.

The heel component 6 continues backwards from the foot component 5 as an integral unit and encloses the heel securely during correction. The cross-sectional shape is shown in FIG. 3. It is shaped like a C tilted backwards on itself. The heel is seated securely in this component during correction, the medial aspect of the heel being held by medial portion 10 and the lateral aspect of the heel by lateral portion 11. The heel is fixated by portion 10 for correction, while portion 11 prevents the heel from going into valgus during correction, a posture to be vigorously prevented.

The leg component 7 extends upwards from the heel comonent 6 as an integral unit. It has a cross-section like an inverted U, and the posterior aspect of the leg or calf rests against it. The angle that the leg component 7 forms with the foot component 5 is not a right angle, but a slightly obtuse angle (plantarflexion or equinus position). Anatomically, dorsiflexion of the ankle and valgus of the heel occur together, while plantarflexion of the ankle occurs with varus of the heel. Holding the ankle in slight plantarflexion therefore helps to prevent valgus of the heel during correction.

The length of the leg component 7 is variable, as long as it is sufficient to keep the heel securely seated in the heel component 6, and to keep the ankle in slight plantarflexion.

Figure 9:
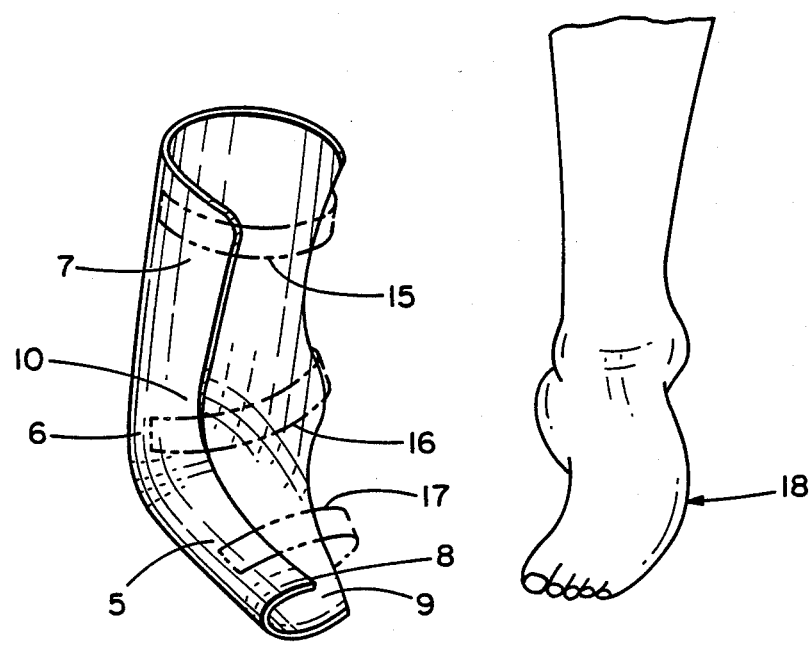
FIG. 9 is a perspective view of the brace with straps, shown alongside the foot to be corrected.

To hold the foot in the brace, strap means 15,16,17 (FIG. 9) are provided which fasten onto the margins of the brace by a velcro touch and grip fastener, although any other adjustable means of fastening would do just as well.

Strap 15 holds the leg to the leg component 7.

Strap 16 holds the heel seated securely in the heel component 6.

Figure 10:
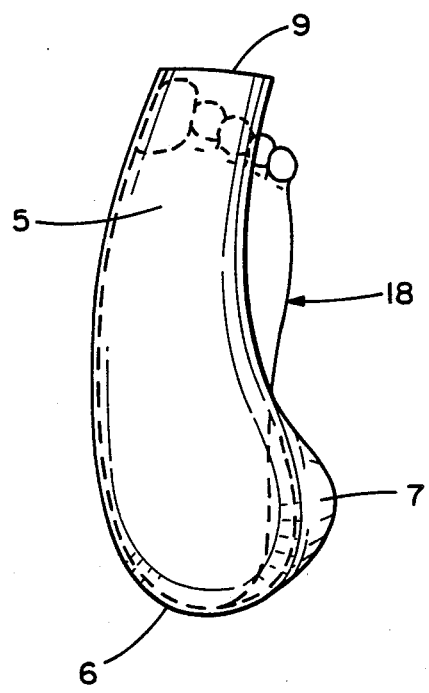
FIG. 10 is a bottom view of the brace with the foot in corrected position.

Strap 17 holds the foot to the foot component 5, but more importantly, it performs the vital task of applying a corrective force on the apex of the convexity 18 (FIG. 9) of the deformity on the lateral border of the foot. With the foot securely held in components 5,6, two points of fixation referred to in the claims as a "static force", have been established at the two ends of the deformity—at the heel and at the base of the big toe, as shown in FIG. 10. The principle of three-point fixation can now be utilized by applying the third point of fixation at the apex of the deformity at 18. This is effected by tightening the adjustable strap against convexity 18, referred to in the claims as a "dynamic force". The amount of correction can be controlled by the tautness of the strap against convexity 18 and this can be carefully graduated over a period of weeks until complete correction is obtained. The usual period for completing correction varies from six weeks to three months.

I claim:

1. A unitary rigid foot brace for the correction of metatarsus adductus in children, for use in combination with a child's foot having a convex deformity on the lateral border thereof, said foot including a big toe, leg and heel, comprising
    a foot component for enclosing and providing a static force at the medial portion of the foot from the heel to, or slightly beyond, the tip of the big toe,
    said foot component having a medial wall C-shaped in cross-sectional configuration, which extends laterally to confine the medial portion of the foot, including the big toe, but not the lateral portion of the foot,
    adjustable strap means for applying a dynamic force at the convexity on the lateral border of the deformed foot to urge the foot into contact with said medial wall and anchor the foot to said component,
    a heel component extending backwards from said foot component for embracing the bottom and both sides of the heel,
    a leg component extending upwardly from said heel component for embracing the lower portion of the leg, and
    adjustable strap means on said leg component to embrace the leg and prevent the heel from pulling away from said heel component.

2. The brace of claim 1 in which said medial wall is curved convexly from heel to toe.

3. The brace of claim 1 which is molded from thermoplastic material and in which said straps are secured by velcro connections.

4. The brace of claim 1 which includes an adjustable strap on said heel component to reinforce the seating of the foot.

5. The brace of claim 1 in which said leg component forms an obtuse angle with said foot component.

6. A unitary rigid foot brace for the correction of metatarsus adductus in children, for use in combination with a child's foot having a convex deformity on the lateral border thereof, said foot including a big toe, leg and heel, comprising
    a foot component shaped to embrace the sole and the top of the foot on the medial side only
    said component extending from the heel to the tip of the big toe to provide a static force at the heel and the big toe, and
    an adjustable strap on said foot component for applying a dynamic force to the convexity on the lateral border of the foot to urge the foot against the resisting static force provided by said foot component at said heel and said tip of the big toe.

* * * * *